(12) United States Patent
Sullivan et al.

(10) Patent No.: US 9,891,175 B2
(45) Date of Patent: Feb. 13, 2018

(54) SYSTEM AND METHOD FOR OBLIQUE INCIDENCE SCANNING WITH 2D ARRAY OF SPOTS

(71) Applicant: KLA-Tencor Corporation, Milpitas, CA (US)

(72) Inventors: Jamie M. Sullivan, Eugene, OR (US); Yevgeniy Churin, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/982,747

(22) Filed: Dec. 29, 2015

(65) Prior Publication Data

US 2016/0327493 A1    Nov. 10, 2016

Related U.S. Application Data

(60) Provisional application No. 62/159,173, filed on May 8, 2015.

(51) Int. Cl.
*G01N 21/00* (2006.01)
*G01N 21/88* (2006.01)
(Continued)

(52) U.S. Cl.
CPC ..... *G01N 21/8806* (2013.01); *G01N 21/9501* (2013.01); *G02B 26/101* (2013.01);
(Continued)

(58) Field of Classification Search
CPC ........... G01N 21/8806; G01N 21/9501; G01N 2201/106; G01N 2201/0668;
(Continued)

(56) References Cited

U.S. PATENT DOCUMENTS 6,236,454 B1    5/2001  Almogy
6,341,006 B1    1/2002  Murayama et al.
(Continued)

FOREIGN PATENT DOCUMENTS

| JP | 2012068232 A | 4/2012 |
|----|----|----|
| KR | 10-0481118 B1 | 9/2005 |
| WO | 2015055387 A1 | 4/2015 |

OTHER PUBLICATIONS

PCT Search Report for Application No. PCT/US2016/030838 dated Jul. 19, 2016, 4 pages.
(Continued)

*Primary Examiner* — Tarifur Chowdhury
*Assistant Examiner* — Isiaka Akanbi
(74) *Attorney, Agent, or Firm* — Suiter Swantz pc llo

(57) ABSTRACT

A system to generate multiple beam lines in an oblique angle multi-beam spot scanning wafer inspection system includes a beam scanning device configured to scan a beam of illumination, an objective lens oriented at an oblique angle relative to the surface of a sample and with an optical axis perpendicular to a first scanning direction on the sample, and one or more optical elements positioned between the objective lens and the beam scanning device. The one or more optical elements split the beam into two or more offset beams such that the two or more offset beams are separated in a least a second direction perpendicular to the first direction. The one or more optical elements further modify the phase characteristics of the two or more offset beams such that the two or more offset beams are simultaneously in focus on the sample during a scan.

28 Claims, 8 Drawing Sheets

(51) Int. Cl.
*G01N 21/95* (2006.01)
*G02F 1/33* (2006.01)
*G02B 27/10* (2006.01)
*G02B 27/12* (2006.01)
*G02B 26/10* (2006.01)

(52) U.S. Cl.
CPC ....... *G02B 27/1086* (2013.01); *G02B 27/123* (2013.01); *G02F 1/33* (2013.01); *G01N 2201/0635* (2013.01); *G01N 2201/104* (2013.01); *G01N 2201/105* (2013.01); *G01N 2201/106* (2013.01)

(58) Field of Classification Search
CPC .............. G01N 2201/0638; G02B 5/32; G02B 26/123; G02B 27/1086; G02B 27/123; G02F 1/33
USPC ............................................ 356/237.2–237.6
See application file for complete search history.

(56) References Cited

U.S. PATENT DOCUMENTS

| | | | |
|---|---|---|---|
| 6,775,051 B2 | 8/2004 | Sullivan et al. | |
| 7,705,331 B1 | 4/2010 | Kirk et al. | |
| 8,194,301 B2 | 6/2012 | Zhao et al. | |
| 8,525,138 B2 | 9/2013 | Smith et al. | |
| 8,698,399 B2 | 4/2014 | Bezel et al. | |
| 8,796,652 B2 | 8/2014 | Bezel et al. | |
| 8,969,841 B2 | 3/2015 | Smith | |
| 8,995,746 B2 | 3/2015 | Cao et al. | |
| 9,048,000 B2 | 6/2015 | Smith | |
| 2007/0188744 A1* | 8/2007 | Leslie | G01N 21/94 356/237.2 |
| 2008/0129988 A1 | 6/2008 | Saito et al. | |
| 2009/0225399 A1* | 9/2009 | Zhao | G01N 21/8806 359/298 |
| 2013/0100525 A1 | 4/2013 | Chiang et al. | |
| 2013/0181595 A1 | 7/2013 | Bezel et al. | |
| 2013/0342105 A1 | 12/2013 | Shchemelinin et al. | |
| 2014/0260640 A1* | 9/2014 | Sullivan | G01N 29/2418 73/655 |

OTHER PUBLICATIONS

Energetiq Technology Inc., EQ-99XFC LDLS™, Compact, Long-Life, High-Brightness, Broadband Laser-Driven Light Source with Fiber-Coupled Output, Found online at <http://www.energetiq.com/DataSheets/EQ99XFC-Data-Sheet.pdf>, © 2014 Energetiq Technology, Inc., 2 pages.

* cited by examiner

SYSTEM AND METHOD FOR OBLIQUE INCIDENCE SCANNING WITH 2D ARRAY OF SPOTS

CROSS-REFERENCE TO RELATED APPLICATION

The present application claims the benefit under 35 U.S.C. §119(e) of U.S. Provisional Application Ser. No. 62/159,173, filed May 8, 2015, entitled OBLIQUE INCIDENCE SCANNING WITH 2D ARRAY OF SPOTS, naming Jamie Sullivan and Yevgeniy Churin as inventors, which is incorporated herein by reference in the entirety.

TECHNICAL FIELD

The present disclosure relates generally to the field of oblique incidence spot scanning wafer inspection systems.

BACKGROUND

Wafer inspection systems are often used to analyze wafers (or "dies") in order to determine the presence of potential defects. A typical wafer inspection system will generate an image of the die to be analyzed and compare this image to a reference image, which may be taken from a database or the image of another die in the series. Spot scanning architectures generate an image of a wafer pixel by pixel by scanning a focused beam of illumination across the sample and detecting light scattered and/or reflected from the sample. In this way, spot scanning systems are capable of detecting features on a wafer with high spatial resolution.

In general, oblique spot scanning wafer inspection systems are configured such that the illumination beam interacts with the wafer at an oblique angle rather than at a normal incidence angle. In the field of wafer inspection systems, oblique angle incidence enables the detection of polarization-induced effects on the sample. Additionally, many surface features such as integrated circuits approximate a diffraction grating; the use of an oblique sampling beam thus enables precise diffraction-based monitoring of wafer features. However, the use of an oblique angle sampling beam in traditional wafer inspection systems may reduce the throughput, or alternatively the efficiency, of a wafer inspection system. This is because only a single linear region may be sampled at a given time. This linear region is described by the intersection of the focal plane of the objective lens, which is typically normal to the optical axis of the objective lens, and the plane of the wafer. A typical oblique angle scanning wafer inspection system will scan an illumination beam along this linear region and detect scattered and reflected light from the sample with one or more detectors. A two-dimensional image is generated through the acquisition of successive line scans in which the sample is moved via a translation stage between successive line scans. Therefore, there exists a critical need to develop systems and methods to increase the throughput of oblique scanning wafer inspection systems.

SUMMARY

A system to generate multiple beam lines in an oblique angle multi-beam spot scanning wafer inspection system is disclosed in accordance with one or more illustrative embodiments of the present disclosure. In one illustrative embodiment, the system includes a beam scanning device configured to scan a beam of illumination. In another illustrative embodiment, the system includes an objective lens positioned to direct the beam to a surface of a sample such that the beam is scanned along a first direction, wherein an optical axis of the objective lens is oriented perpendicular to the first direction and is further oriented at an oblique incidence angle relative to a surface of the sample. In another illustrative embodiment, the system includes one or more optical elements positioned between the objective lens and the beam scanning device. In one illustrative embodiment, the one or more optical elements are configured to split the beam into two or more offset beams, wherein the two or more offset beams are separated in at least a second direction, wherein the second direction is perpendicular to the first direction. In another illustrative embodiment, the one or more optical elements are configured to modify the phase characteristics of the two or more offset beams such that the two or more offset beams are simultaneously in focus on the sample during a scan.

An apparatus for the generation of spots on an inclined surface is disclosed in accordance with one or more illustrative embodiments of the present disclosure. In one illustrative embodiment, the apparatus includes one or more optical elements positionable in a beam scanning system prior to an objective lens oriented at an oblique angle relative to a surface, and wherein an optical axis of the lens is perpendicular to a first direction on a plane defined by the surface. In one illustrative embodiment, the one or more optical elements are configured to split a beam into two or more offset beams, wherein the two or more offset beams are separated in at least a second direction, wherein the second direction is perpendicular to the first direction. In another illustrative embodiment, the one or more optical elements are configured to modify the phase characteristics of the two or more offset beams such that the two or more offset beams are simultaneously in focus on the surface during a scan.

A method for generating multiple beams in an oblique multi-beam spot scanning wafer inspection system is disclosed in accordance with one or more illustrative embodiments of the present disclosure. In one illustrative embodiment, the method includes generating a beam of illumination. In another illustrative embodiment, the method includes directing the beam to a surface at an oblique angle, wherein the beam is substantially perpendicular to a first direction on a plane defined by the surface. In another illustrative embodiment, the method includes prior to directing the beam, splitting the beam into two or more offset beams, wherein the two or more offset beams are separated in at least a second direction, and wherein the second direction is perpendicular to the first direction. In another illustrative embodiment, the method includes prior to directing the beam, modifying the phase characteristics of the two or more offset beams such that the two or more offset beams are simultaneously in focus on the surface.

Figure 3A:
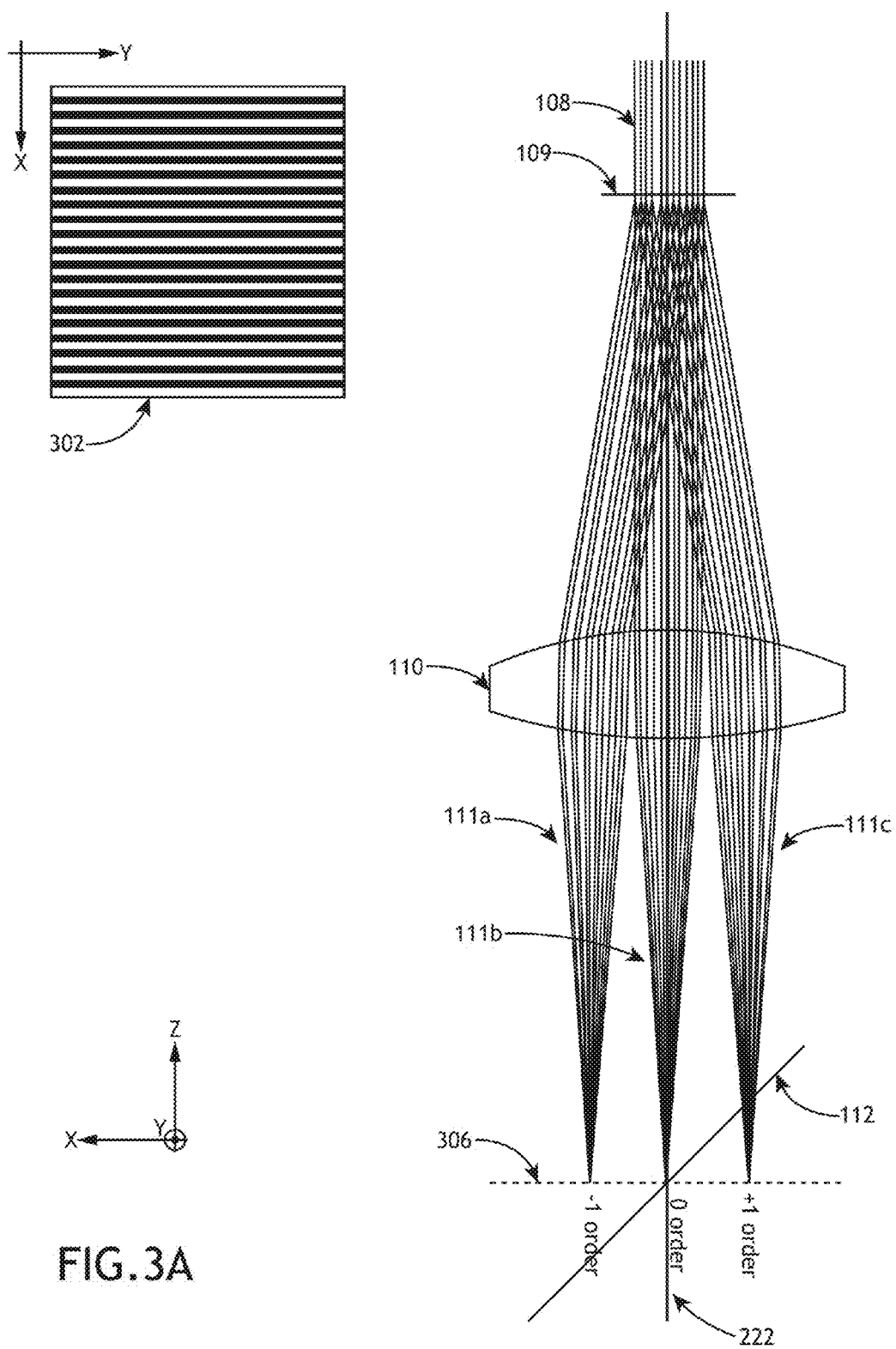
FIG. 3A is a simplified schematic of a diffraction grating generating three beams formed from the −1, 0, and +1 diffraction orders that are not properly focused on a wafer, in accordance with one embodiment of the present disclosure.
Figure 3B:
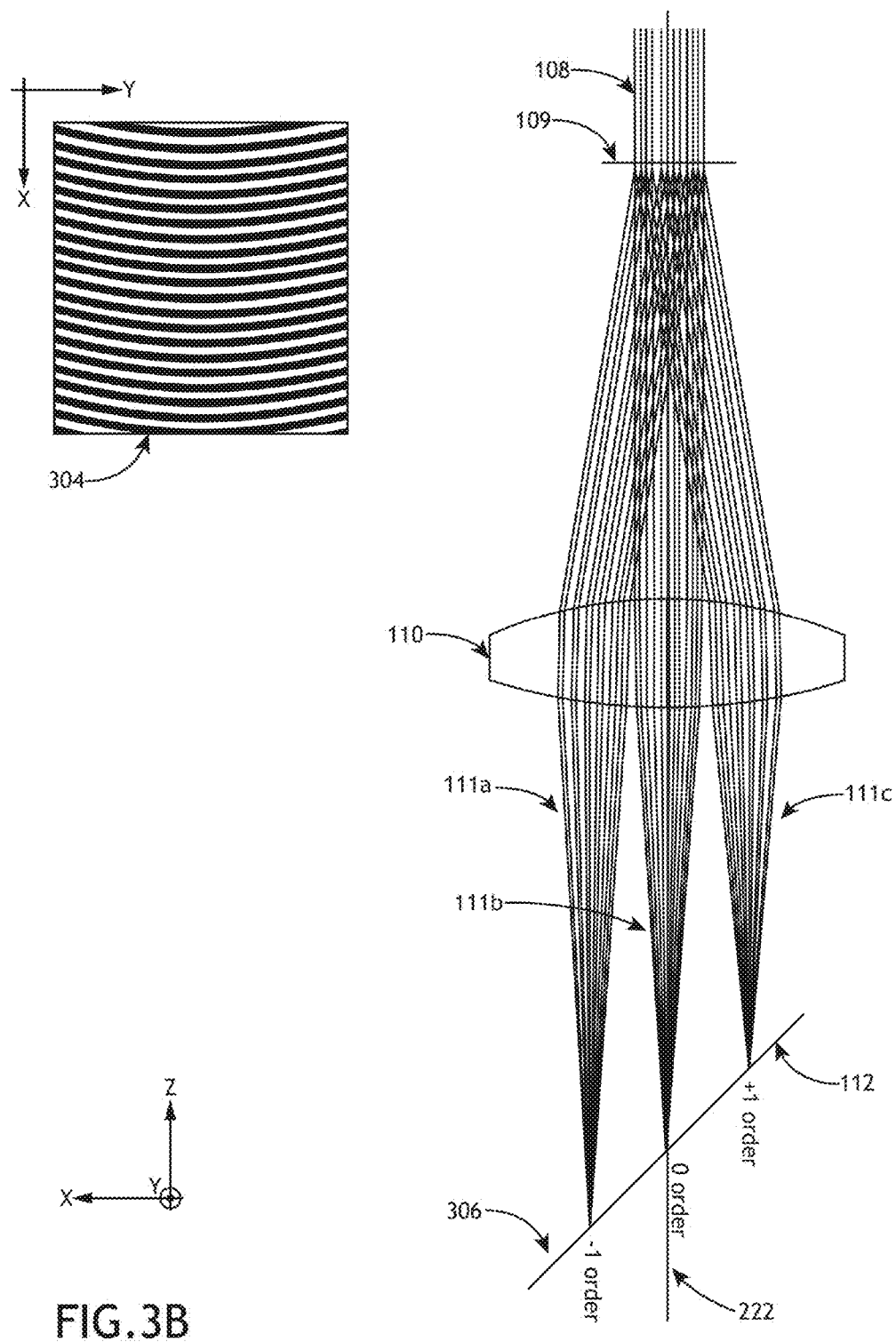

FIG. 3B is a schematic diagram of a diffraction grating with defocus generating three beams formed from the −1, 0, and +1 diffraction orders that are properly focused on a wafer, in accordance with one embodiment of the present disclosure.

Figure 3C:
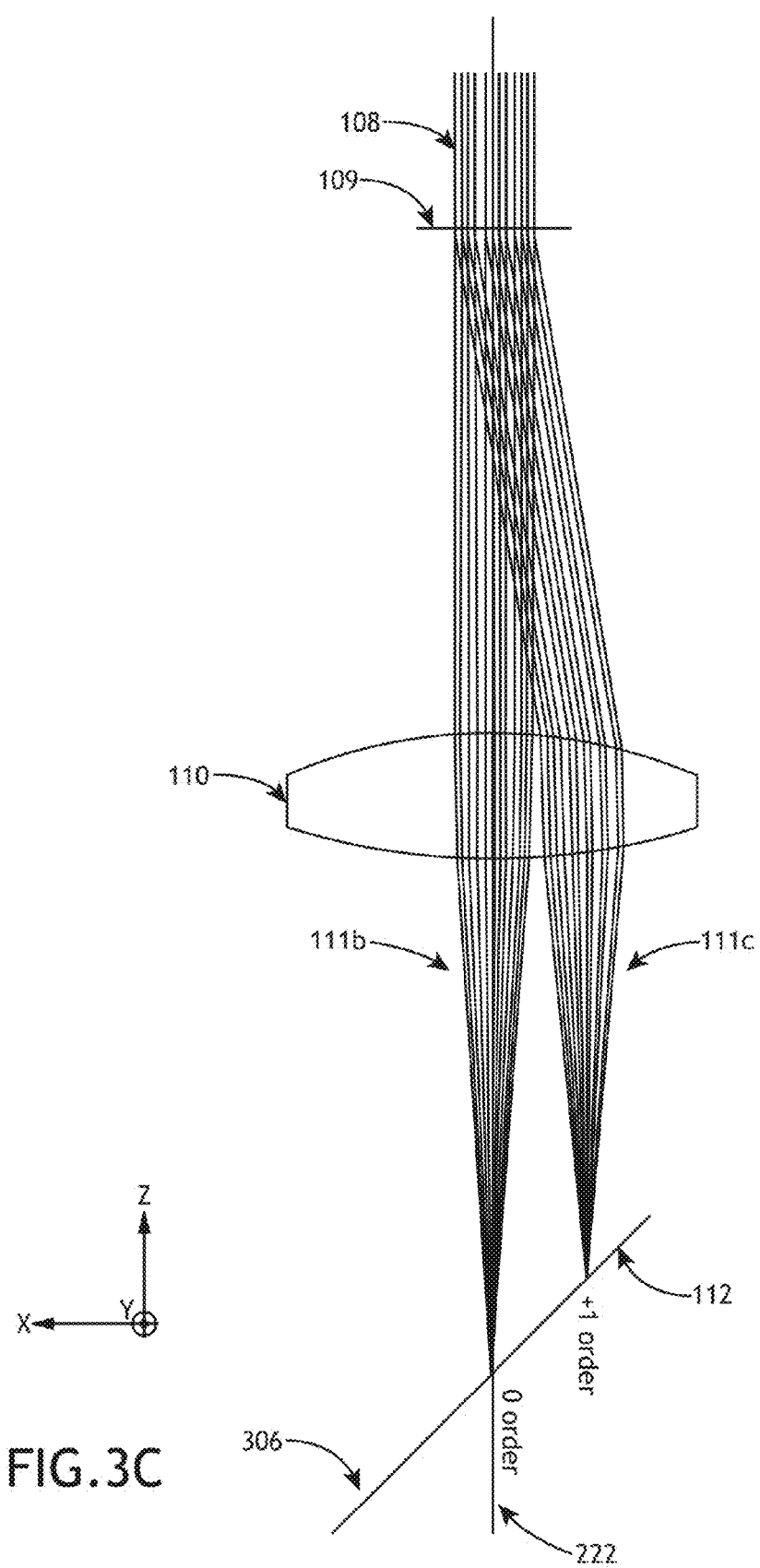

FIG. 3C is a schematic diagram of a diffraction grating with defocus generating two beams formed from the 0 and +1 diffraction orders that are properly focused on a wafer, in accordance with one embodiment of the present disclosure.

Figure 3D:
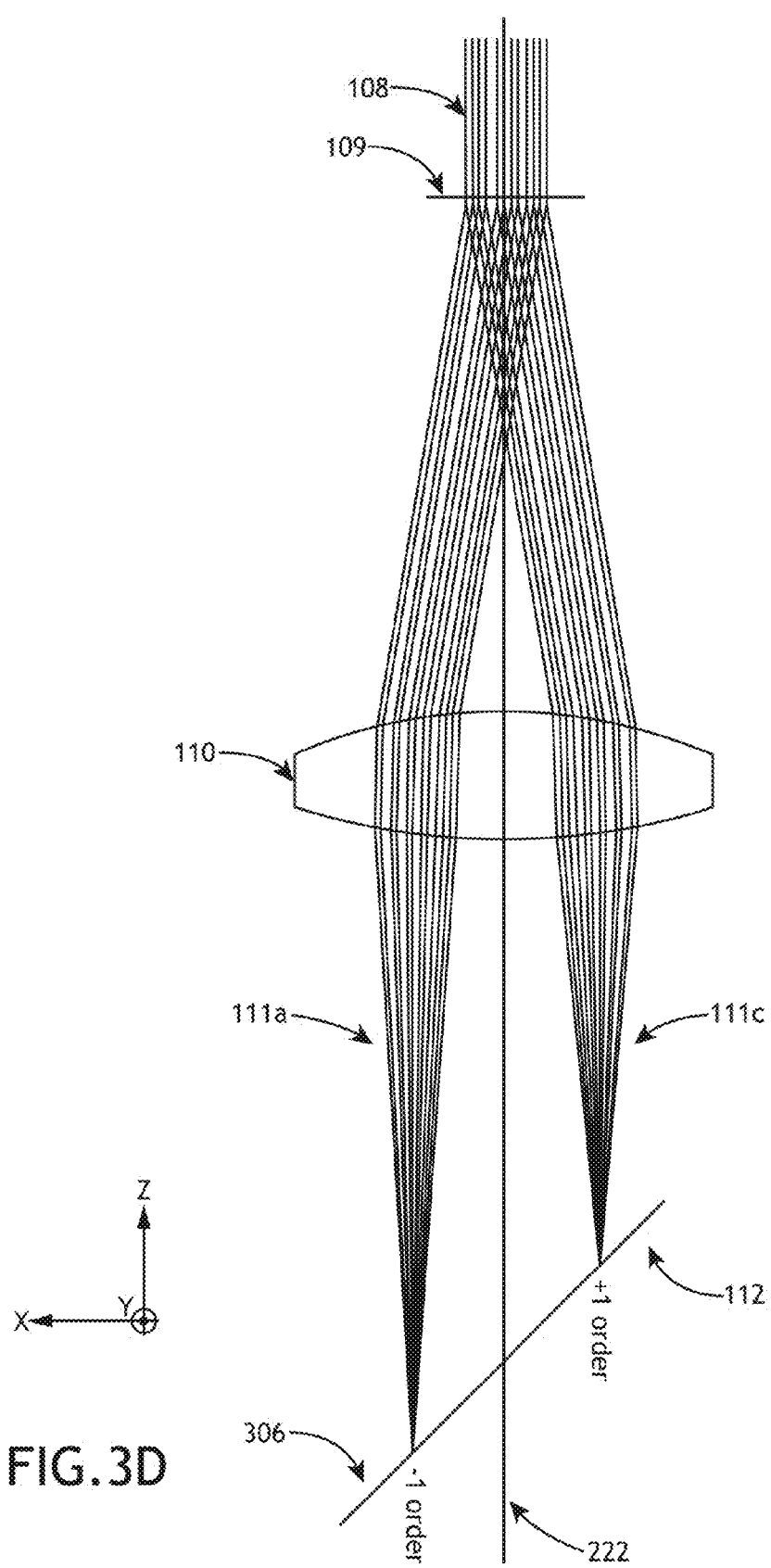

FIG. 3D is a schematic diagram of a diffraction grating with defocus generating two beams formed from the −1 and +1 diffraction orders that are properly focused on a wafer, in accordance with one embodiment of the present disclosure.

Figure 4B:
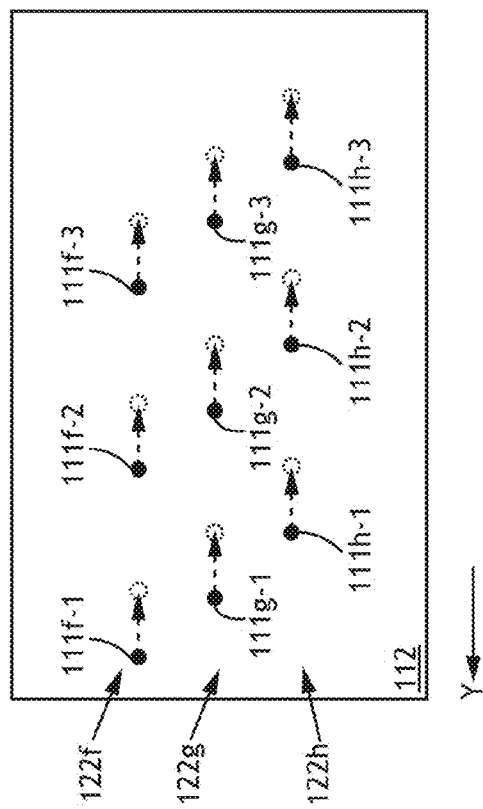
Figure 4A:
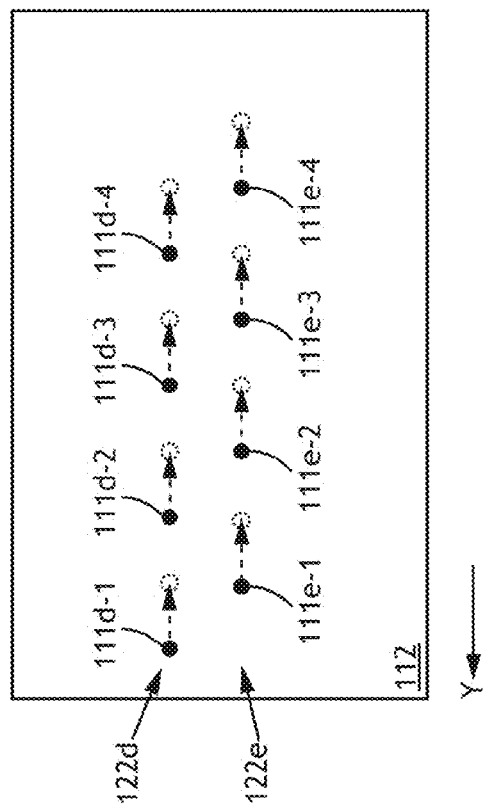

FIG. 4A is a simplified schematic of a scan pattern with two sets of four beams oriented along two scan lines simultaneously in focus on a wafer, in accordance with one embodiment of the present disclosure.

FIG. 4B is a simplified schematic of a scan pattern with three sets of three beams oriented along three scan lines simultaneously in focus on a wafer, in accordance with one embodiment of the present disclosure.

Figure 5:
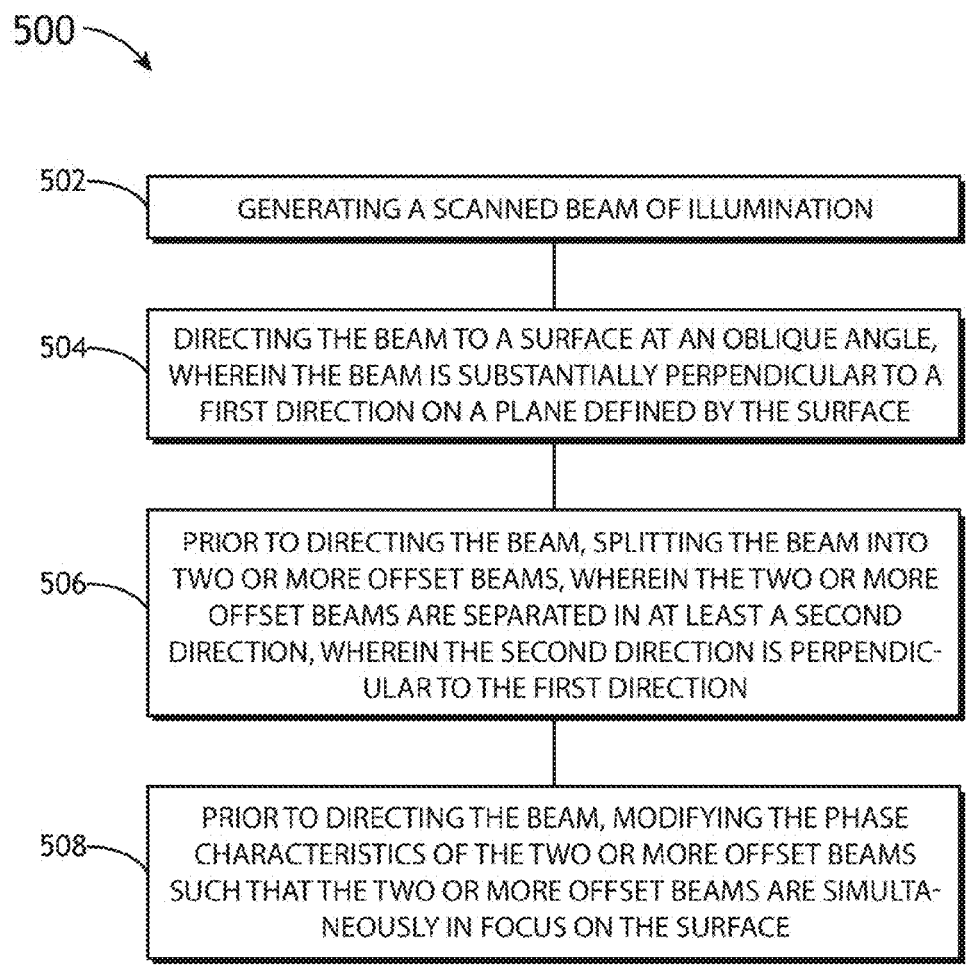

FIG. 5 is a flow diagram illustrating a method for generating multiple beams in an oblique multi-beam spot scanning wafer inspection system, in accordance with one embodiment of the present disclosure.

DETAILED DESCRIPTION

Reference will now be made in detail to the subject matter disclosed, which is illustrated in the accompanying drawings. The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Referring generally to FIGS. 1 through 5, systems and methods for scanning a wafer with multiple parallel beams at an oblique incidence angle are described in accordance with one or more embodiments of the present disclosure. Embodiments of the present disclosure are directed to the generation of multiple beams simultaneously focused onto a wafer in an oblique incidence spot scanning wafer inspection system. In one embodiment, one or more optical elements 109 (e.g. one or more diffractive optical elements (DOEs)) separates a beam into two or more offset beams 111 located along two or more scan lines 122. The one or more optical elements 109 are further arranged so as to modify the phase of the two or more offset beams 111 such that the two or more offset beams 111 located along two or more scan lines 122 are simultaneously in focus on the wafer after being focused by an objective lens 110. In this regard, the one or more optical elements 109 rotate the focal plane 306 of the two or more offset beams 111 to match the sample orientation. A spot scanning wafer inspection system is generally described in U.S. Pat. No. 6,775,051 issued on Aug. 8, 2004; and U.S. Pat. No. 8,995,746 issued on Mar. 31, 2015; which are incorporated herein by reference in their entirety. Multi-spot scanning wafer inspections are generally described in U.S. Pat. No. 6,236,454 issued on May 22, 2001; and U.S. Pat. No. 8,194,301 issued on Jun. 5, 2012; which are incorporated herein by reference in their entirety.

It is noted that a given wafer inspection system may detect defects on a wafer through the acquisition of an image of the wafer and the comparison of this image to a reference image. A spot scanning imaging system generates an image of a wafer pixel-by-pixel by scanning illumination from an illumination source (e.g. a laser) across the wafer and collecting illumination from the wafer from discrete locations on the wafer. It is noted herein that illumination may be collected from the wafer using one or more detectors. It is further noted that the physical location of the sampled points defines a grid of sampled points (i.e. a sampling grid) and further defines the pixels of the image. The combination of point-by-point detection and the use of one or more detectors to gather information from each sampled point enables the generation of highly resolved and highly sensitive images.

Figure 1:
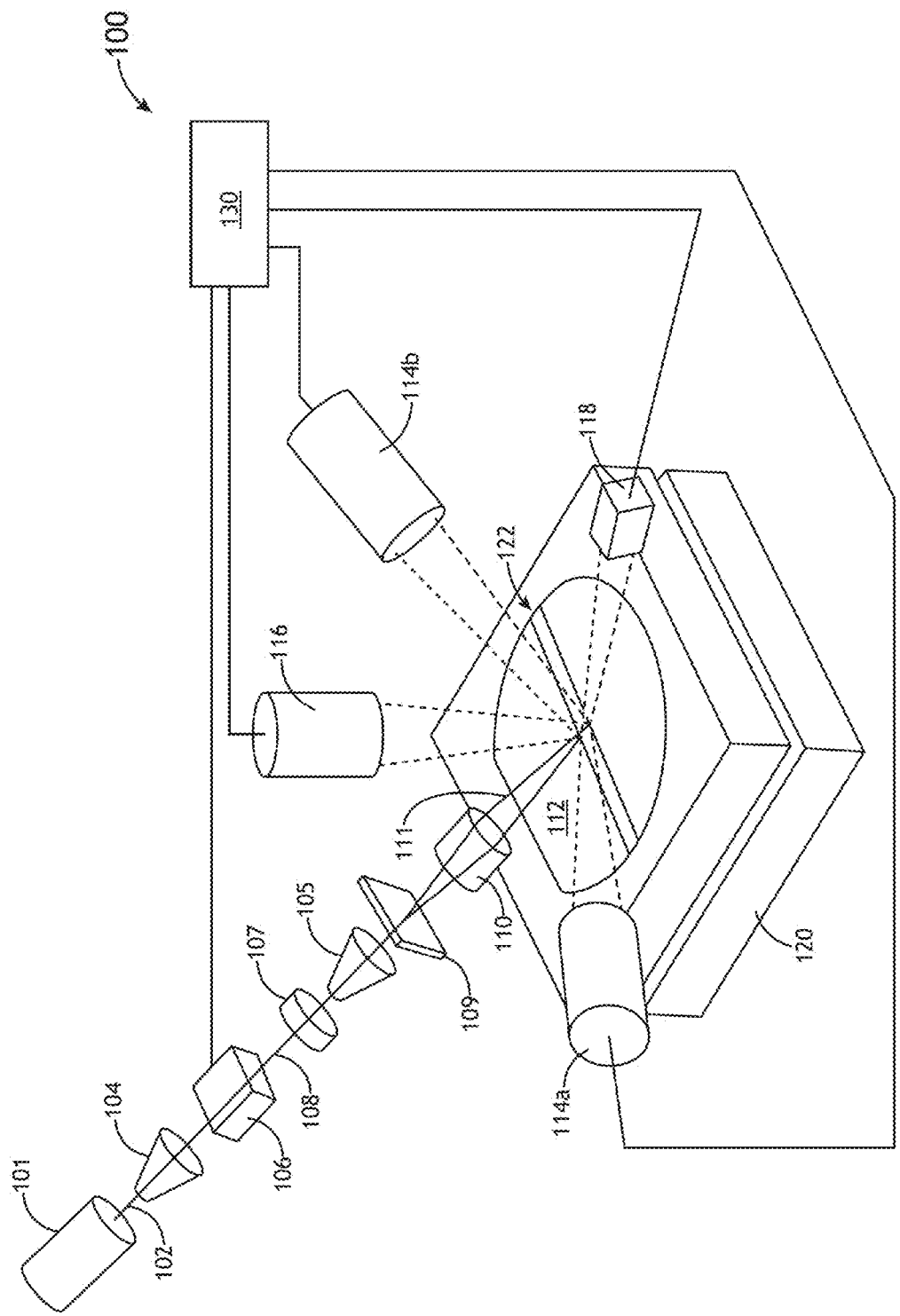
FIG. 1 is a schematic view of an oblique incidence multi-beam spot scanning wafer inspection system, in accordance with one embodiment of the present disclosure.
Figure 2:
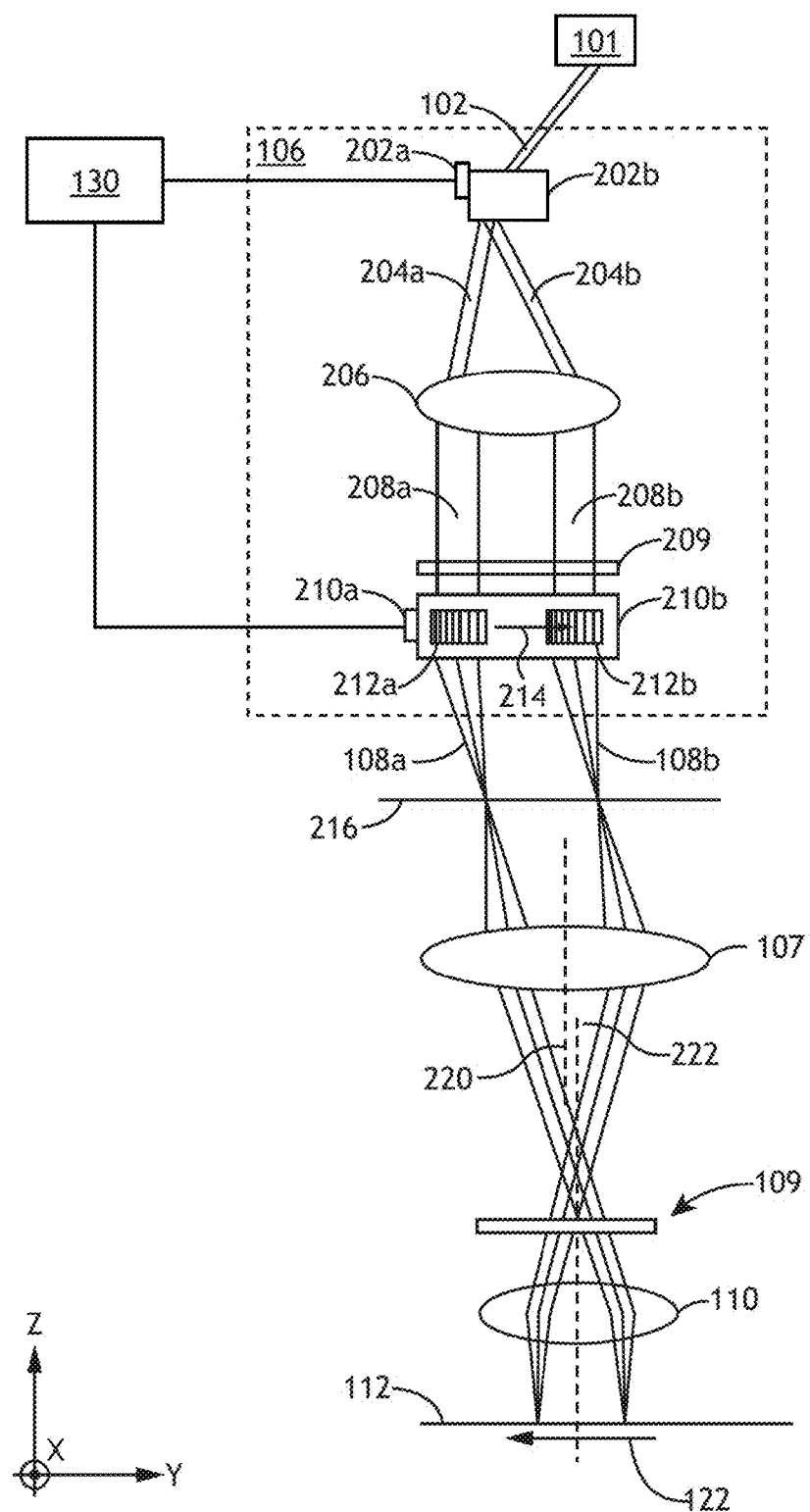
FIG. 2 is a schematic view of a portion of an oblique incidence multi-beam spot scanning wafer inspection system illustrating the use of acousto-optic deflectors to linearly scan a beam and an optical element to modify the focal characteristics of the beam, in accordance with one embodiment of the present disclosure.

FIGS. 1-3 illustrate a wafer inspection system 100 in which two or more offset beams 111 are scanned along two or more scan lines 122 on a wafer 112 oriented at an oblique angle relative to an objective lens 110, in accordance with one or more embodiments of the present disclosure. It is noted that the speed or throughput of an oblique angle scanning inspection system with multiple parallel scan lines 122 is increased relative to a system in which all beams lie on a single scan line. In one embodiment, an illumination source 101 generates a beam of illumination 102. In another embodiment, a beam scanner 106 transforms the beam 102 into a scanning beam 108. In another embodiment, an objective lens 110 collects the scanning beam 108. In another embodiment, one or more optical elements 109 (e.g. a diffractive optical element) are positioned prior to the objective lens 110. In another embodiment, the one or more optical elements 109 split the scanning beam 108 into two or more offset beams 111 separated in at least the x-direction. Further, the one or more optical elements 109 may rotate the focal plane 306 of the two or more offset beams 111 focused by the objective lens 110 to match the surface of the wafer 112. It is noted herein that the rotation of the focal plane 306 of the two or more offset beams 111 focused by the objective lens 110 enables the two or more offset beams 111 located on two or more scan lines 122 to be in focus at all points during a scan. Without the rotation of the focal plane 306 of the two or more offset beams 111, the focal plane 306 of the two or more offset beams 111 would be oriented normal to the optical axis of the objective lens 110 and would intersect with the wafer 112 along a single linear intersection region.

In one embodiment, one or more beam conditioning elements 104 are positioned prior to the beam deflector 106. The one or more beam conditioning elements 104 may include any optical element known in the art suitable for conditioning the beam 102. For example, the one or more beam conditioning elements 104 may include, but are not limited to, one or more lenses, one or more polarizers, one or more filters, one or more waveplates, or one or more beam shapers. In one embodiment, the one or more beam conditioning elements 104 expand the beam 102 to fill an input aperture of a beam scanner 106. In another embodiment, the one or more beam conditioning elements 104 adjust the polarization of the beam 102. In another embodiment, the one or more beam conditioning elements 104 modify the spatial profile of the beam 102. For example, the one or more beam conditioning elements 104 may be configured such that the spot size of each of the two or more offset beams 111 is constant and independent of the location on the wafer 112.

In another embodiment, the system 100 includes a relay lens 107 positioned after the beam deflector 106 to collect the beam 108. For example, a relay lens 107 may collimate a focused scanning beam 108 directed from a beam scanner 106 and direct the collimated scanning beam 108 to the one or more optical elements 109. In one embodiment, one or more beam conditioning elements 105 are positioned prior to the objective lens 110. The one or more beam conditioning elements 105 may include any optical element known in the art suitable for conditioning the scanning beam 108. For example, the one or more beam conditioning elements 105 may include, but are not limited to, one or more lenses, one or more magnification controllers, one or more polarizers, one or more filters, one or more waveplates, or one or more beam shapers. In one embodiment, the one or more beam conditioning elements 105 includes a magnification controller suitable for adjusting the focused size of the two or more offset beams 111 on the wafer 112. It is noted herein that the one or more beam conditioning elements 105 may be positioned either prior to or subsequent to the one or more optical elements 109. It is further noted that the one or more optical elements 109 may be positioned between two beam conditioning elements 105.

In another embodiment, the system 100 includes a stage assembly 120 suitable for securing and positioning a wafer 112. The stage assembly 120 may include any sample stage architecture known in the art. By way of a non-limiting example, the stage assembly 120 may include a linear stage. By way of another example, the stage assembly 120 may include a rotational stage. The wafer 112 may include a wafer, such as, but not limited to, an unpatterned semiconductor wafer. It is noted herein that a two-dimensional image of a wafer 112 may be generated by translating the wafer 112 between successive scans along the two or more scan lines 122. It is further noted that the one or more beam deflectors 106 can include any type of beam deflectors known in the art including, but not limited to, acousto-optic beam deflectors, electro-optic beam deflectors, a polygonal scanner, a resonant scanner, or a galvanometer scanner.

It is noted herein that the illumination source 101 may include any illumination source known in the art. For example, the illumination source 101 may include, but is not limited to, any laser system, including one or more laser sources, configured to generate a set of wavelengths or a wavelength range. The laser system may be configured to produce any type of laser radiation such as, but not limited to infrared radiation, visible radiation and/or ultraviolet (UV) radiation. In one embodiment, the illumination source 101 is a laser system configured to emit continuous wave (CW) laser radiation. In another embodiment, the illumination source 101 is a pulsed laser source. In another embodiment, the illumination source 101 is configured to produce a modulated output. For example, the illumination source 101 may be modulated with an acousto-optic or an electro-optic modulator to produce temporally shaped illumination.

In another embodiment, the illumination source 101 includes one or more excimer laser systems. For example, the illumination source may include, but is not limited to, an excimer laser with molecular fluorine as an active gas, which provides emission of 157 nm laser light. In another embodiment, the illumination source 101 includes one or more diode laser systems (e.g., one or more diodes for emitting light at 445 nm).

In one embodiment, the illumination source 101 includes one or more diode lasers. In another embodiment, the illumination source 101 includes one or more diode-pumped solid state lasers. For example, the illumination source 101 may include a diode-pumped solid state laser with a wavelength including, but not limited to 266 nm. In another embodiment, the illumination source 101 includes one or more frequency converted laser systems. For instance, the illumination source 101 may include, but is not limited to, a frequency converted laser suitable for emitting light having a nominal central illumination wavelength of 532 nm coupled with a frequency-doubling system that produces illumination with a 266 nm central wavelength.

In one embodiment, one or more multi-channel detectors are positioned to simultaneously collect reflected and/or scattered light from two or more scan lines 122 on the wafer 112. In one embodiment, a detector 118 is positioned to receive laser light reflected from the wafer 112. The detector 118 may operate as a "reflectivity sensor" or a "brightfield sensor". For example, the detector 118 may be used to generate a reflectivity map of the sample. As another example, the detector 118 may be used to monitor wafer 112 characteristics including, but not limited to, structure height, film thickness, or dielectric constant. In another embodiment, a detector 116 is positioned normal to the surface of the wafer 112 to detect light scattered in a direction normal to the wafer surface. Additionally, a detector 116 may detect light directly reflected from structures on the wafer surface. In one embodiment, detectors 114a and 114b detect light scattered from two or more scan lines 122. In this regard, one or more detectors 114 may collect forward scattered light, laterally scattered light, or backward scattered light according the detector position relative to the sampled point. It is noted herein that the one or more detectors 114a, 114b, 116 or 118 may include any detector known in the art. For example, detectors 114a, 114b, 116 or 118 may include, but are not limited to, a CCD detectors, photodiodes, avalanche photodiodes (APDs) and/or or photomultiplier tubes (PMTs). It is further noted that the one or more detectors 114a, 114b, 116 or 118 may be multi-channel detectors configured to simultaneously detect signals from multiple detection regions on the wafer 112 (e.g. one or more regions of one or more scan lines 122). It is contemplated herein that cross-talk between channels of a detector (e.g. 114a, 114b, 116 or 118) may be minimized by separating the detection regions on a wafer 112 such that illumination (e.g. scattered light) from a given detection region is only detected by a single channel.

In one embodiment, the system 100 includes a controller 130 configured to transmit driving signals to the stage assembly 120, the one or more beam deflectors 106, and detectors 114a, 114b, 116, and 118 in order to initiate the linear sweep of the beam 108 across the wafer 112, the sampling of illumination scattered and/or reflected from the wafer 112, and the movement of the wafer 112 by the stage assembly 120. An image of a linear region of the wafer 112 is generated by triggering the one or more detectors 114a, 114b, 116, and/or 118 at one or more locations on the sample as the two or more offset beams 111 are swept across the wafer 112. In one embodiment, a two-dimensional image of the wafer 112 may be generated by translating by the stage assembly 120 in a direction orthogonal to the beam scan direction such that each linear scan may be performed on a new location of the wafer 112. It is noted herein that the sampling grid of the wafer may be defined by both the sampling rate of the detectors as well as the translation of the stage assembly 120. In another embodiment, one or more linear scans may be performed on a single location of the wafer 112 before translation to a new location. Multiple beam scans may be desirable, for example, to reduce system noise.

The accuracy of a spot scanning wafer inspection system may be further improved by run-time alignment of the sample grid of a wafer 112 to the sample grid of a reference image or with respect to previous scan data. For example, run-time alignment of the sample grid of a wafer 112 based on data associated with the previous scans (e.g. the previous 200 scanned rows) may improve scan accuracy. The sample grid of the wafer 112 may become misaligned relative to the sample grid of a reference image as a result of multiple factors, including, but not limited to, original alignment errors when positioning a wafer 112 with a stage assembly 120, mechanical vibrations, air wiggle, air currents, and/or drift of the two or more offset beams 111.

Referring now to FIG. 2, a beam scanner 106 includes a beam deflector 202 and an accousto-optic deflector 210, in accordance with one or more embodiments of the present disclosure. It is noted herein that for the purposes of the present disclosure, the terms "beam scanner" and "beam deflector" are used interchangeably. In one embodiment, a beam 102 is generated by the illumination source 101 and is incident on a beam deflector 202 communicatively coupled to the controller 130. The beam deflector 202 sweeps the beam 204 directed from the beam deflector 202 across a range of angles that define an angular spread. For example, the beam deflector 202 deflects a beam in a first position 204a to a second position 204b. The beam deflector 202 may include any beam deflector known in the art. For example, the beam deflector 202 may be formed from, but is not limited to, an acousto-optic deflector, an electro-optic deflector, a polygonal deflector, a resonant deflector, or a galvanometer deflector. In one embodiment, the beam deflector 202 is an acousto-optic deflector consisting of a solid medium 202b coupled with a transducer 202a configured to generate ultrasonic waves that propagate through the solid medium 202b. Properties of the solid medium 202b such as, but not limited to, the refractive index are modified by the propagating ultrasonic waves such that the beam 102 is deflected upon interaction with the solid medium 202b according to the wavelength of the ultrasonic waves. Furthermore, the ultrasonic waves propagate through the solid medium 202b at the velocity of sound in the medium and have a wavelength related to the frequency of the drive signal as well as the velocity of sound in the solid medium 202b. In one embodiment, the transducer 202a generates ultrasonic waves in response to a drive signal generated by a controller 130.

In one embodiment, a lens assembly 206 translates the angular sweep of the beam 204 to a linear sweep of the beam 208 directed from the lens assembly 206. In another embodiment, a lens 206 collimates the beam. In another embodiment, the one or more lenses 206 modify the spatial profile of the beam 204. In another embodiment, the lens assembly 206 expands the diameter of the beam 204.

In one embodiment, the beam 204 is directed to an acousto-optic deflector 210 configured as a traveling lens. A transducer 210a communicatively coupled to the controller 130 generates a chirp packet 212 of ultrasonic waves with linearly varying frequency that propagates through a solid medium 210b along a linear path 214. The chirp packet 212 operates as a traveling cylindrical lens such that a beam 208 incident on the chirp packet 212 is focused to a position on a line 216; portions of a light beam 208 incident on relatively low frequency portions of the chirp packet 212 are deflected less than portions of a light beam 208 incident on relatively high frequency portions of the chirp packet 212. In one embodiment, a cylindrical lens 209 focuses the scanning beam 108 in a plane orthogonal to the direction of focus induced by the chirp packet 212. In this regard, the axis of the cylindrical lens 209 is oriented parallel to the scan direction 214. A cylindrical lens 209 may be placed either before the acousto-optic deflector 210 (e.g. as shown in FIG. 2) or directly after the acousto-optic deflector 210. In one embodiment, the position and rate of the linear sweep of beam 208 are synchronized with the propagation of a chirp packet 212. In this way, a beam 208a may be incident on a travelling chirp packet 212a; as the chirp packet 212 propagates from position 212a to 212b, the beam 208a correspondingly propagates from position 208a to position 208b. As a result, a scanning beam 108 directed from a chirp packet 212 is focused on and linearly scanned along a line 216. It is noted herein that the width of a chirp packet 212 may be less than the length of the solid medium 210b. It is further noted that multiple chirp packets 212 may propagate through the solid medium 210b at the same time in sequence.

In another embodiment, the beam scanner 106 is formed from a lens and a single accousto-optical deflector 210 operating in "flood mode". In this regard, the lens 206 expands the beam 102 and illuminates the full length of the accousto-optical deflector 210 with a stationary beam 208. One or more propagating chirp packets 212 may then be continually illuminated by a portion of the stationary beam 208; portions of the beam 208 not incident on the one or more propagating chirp packets 212 remain unfocused by the accousto-optical deflector 210.

In one embodiment, a lens 107 collimates the scanning beam 108 and an objective lens 110 focuses the scanning beam 108 onto the wafer 112. In one embodiment, the relay lens 107 and the objective lens 110 are positioned in a telecentric configuration. In another embodiment, the relay lens 107 and the objective lens 110 share a common optical axis. In another embodiment, the optical axis 222 of the objective lens 110 is shifted from, but parallel to, the optical axis 220 of the relay lens 107. In this way, the optical axis 222 of the objective lens 210 may be centered on the scan line 122 of the focused scanning beam 108 on the wafer 112. It is noted that all optical rays in FIG. 2 lie on the y-z plane, and that the two or more scan lines 122 are oriented in the y-direction and separated in the x-direction. It is further noted that one or more optical elements 109 positioned prior to the objective lens 110 may split the scanning beam 108 into two or more offset beams 111 separated along the x-direction in order to generate additional scan lines 122 not on the y-z plane.

Referring now to FIGS. 3A-3D, one or more optical elements 109 positioned prior to the objective lens 110 simultaneously split the beam 108 into two or more offset beams 111 and rotate the focal plane 306 of the two or more offset beams 111 to overlap the surface plane of the sample 112, in accordance with one or more embodiments of the present disclosure. The one or more optical elements 109 may be formed from any type in the art suitable for splitting the beam 108 and rotating the focal plane 306. For example, the one or more optical elements 109 may include, but are not limited to, one or more diffractive optical elements, one or more refractive optical elements, or one or more beam splitters. Furthermore, the one or more optical elements 109 may operate in either transmission or reflection mode. In one embodiment, the one or more optical elements 109 include one or more holographic DOEs. In another embodiment, the one or more optical elements 109 include one or more micro-lens assemblies.

In one embodiment, an optical element 109 is formed from a DOE configured as a diffraction grating with focus correction (e.g. defocus) such that one or more diffracted orders are generated along the x direction and the focal plane 306 of the diffracted orders are simultaneously in focus on the wafer 112. Referring to FIG. 3A, an optical element 109 consisting of a diffraction grating without focus correction 302 will generate three offset beams 111a, 111b, and 111c (i.e. diffracted orders) separated in the x-direction that are focused through the objective lens 110 to a focal plane 306 oriented perpendicular to an optical axis 222 rather than the plane of the wafer 112. Thus, only one of the three offset beams 111 may be in focus on the wafer 112. Referring now to FIG. 3B, an optical element 109 consisting of a diffraction grating with focus correction 304 will effectively tilt the focal plane 306 of the three offset beams 111a, 111b, and 111c through the objective lens 110 such that the focal plane 306 overlaps the surface plane of the wafer 112. In this way, the three offset beams 111a, 111b, and 111c are simultaneously in focus on the wafer 112. It is noted that each of the three offset beams 111a, 111b, and 111c may be scanned along separate scan lines 122 in the y-direction and remain in focus during the scan.

It is noted herein that defocus is a second order aberration and is described by a wavefront aberration function of $W_{020}r^2$, or alternatively $W_{020}(x^2+y^2)$. In one embodiment, an optical element 109 is configured as a diffraction grating with defocus such that the optical phase delay of an incident beam 108 is modified according to the equation:

$$\phi = K\left[\frac{2\pi}{T}x + A(x^2 + y^2)\right]$$

where K=0, ±1, ±2, . . . is the diffraction order, T is the period of the grating, and A is an amplitude term representing the degree of defocus. In this manner, the DOE operates as a phase mask to simultaneously split the scanning beam 108 into two or more offset beams 111 and modify the phase characteristics of the two or more offset beams 111 such that all offset beams 111 are simultaneously in focus on the wafer 112 through the objective lens 110. Further, the value of A may be chosen to adjust the rotation of the focal plane 306 to overlap the surface plane of the wafer 112.

It is noted herein that the two or more offset beams 111 may include any number of beams. It is further noted that offset beams 111 may be generated from any combination of diffracted orders from an optical element 109. FIG. 3C illustrates the formation of a first offset beam 111b formed from the 0 (undiffracted) order of an optical element 109 and a second offset beam 111c formed from the +1 diffraction order of an optical element 109, in accordance with one or more embodiments of the present disclosure. FIG. 3D illustrates the formation of a first offset beam 111a formed from the −1 order of an optical element 109 and a second offset beam 111c formed from the +1 diffraction order of an optical element 109, in accordance with one or more embodiments of the present disclosure. It is further noted that increased separation between scan lines may reduce cross-talk between adjacent channels in a multi-channel detector (e.g. 114a, 114b, 116, or 118). In another embodiment, the two or more offset beams 111 associated with diffracted orders generated by an optical element 109 are selected with one or more irises in the system 100.

It is noted herein that the one or more optical elements 109 may further split the beam 108 into multiple offset beams separated along the y-direction. In this way, a two-dimensional array of offset beams 111 may be in focus on the wafer 112 during a scan. In one embodiment, one or more optical elements 109 split the beam 108 into a two-dimensional array of offset beams 111 with two or more staggered rows, wherein the rows are oriented along the y-direction (e.g. the scan direction). It is noted herein that a staggered row configuration enables increased separation between beams in adjacent rows in order to reduce cross-talk between adjacent channels in a multi-channel detector (e.g. 114a, 114b, 116, or 118).

FIGS. 4A and 4B illustrate two non-limiting examples of scan patterns on the surface of a wafer 112, in accordance with two or more embodiments of the present disclosure. FIG. 4A illustrates a scan pattern on a wafer 112 in which offset beams 111 are arranged in a 2×4 array with staggered rows, in accordance with one or more embodiments of the present disclosure. In this way, a first row of offset beams 111d includes a set of four beams 111d-1, 111d-2, 111d-3, and 111d-4; and a second row of offset beams 111e includes a set of four beams 111e-1, 111e-2, 111e-3, and 111e-4. The arrows represent the scan lines 122 (e.g. 122d and 122e) of the offset beams 111. It is noted herein that each of the offset beams 111 are separated in the y-direction as well as the direction perpendicular to the y-direction on the sample in order to minimize cross-talk. It is further noted that all offset beams 111 are simultaneously in focus on the surface of the wafer 112 during the length of each scan path. In one embodiment, the offset beams 111d located on scan line 122d are formed from a 0 (undiffracted) order of an optical element 109, and the offset beams 111e located on scan line 122e are formed from a +1 diffraction order of an optical element 109. In another embodiment, the offset beams 111d located on scan line 122d are formed from a −1 diffraction order of an optical element 109, and the offset beams 111e located on scan line 122e are formed from a +1 diffraction order of an optical element 109.

FIG. 4B illustrates a scan pattern on a wafer 112 in which offset beams 111 are arranged in a 3×3 array with staggered rows, in accordance with one or more embodiments of the present disclosure. In this way, a first row of offset beams 111f includes a set of three beams 111f-1, 111f-2, and 111f-3; a second row of offset beams 111g includes a set of three beams 111g-1, 111g-2, and 111g-3; and a third row of offset beams 111h includes a set of three beams 111h-1, 111h-2, and 111h-3. The arrows represent the scan lines 122 (e.g. 122f, 122g, and 122h) of the offset beams 111. It is noted herein that each of the offset beams 111 are separated in the y-direction as well as the direction perpendicular to the y-direction on the sample in order to minimize cross-talk. It is further noted that all offset beams 111 are simultaneously in focus on the surface of the wafer 112 during the length of each scan path. In one embodiment, the offset beams 111f located on scan line 122f are formed from a −1 diffraction order of an optical element 109, the offset beams 111g located on scan line 122g are formed from a 0 (undiffracted) order of an optical element 109, and the offset beams 111h located on scan line 122h are formed from a +1 diffraction order of an optical element 109.

It is noted herein that FIGS. 4A and 4B and the corresponding description provided above are provided merely for illustrative purposes and should not be interpreted as a limitation on the present disclosure. As such, scan patterns may include any number of beams arranged in any orientation such that the scan beams are simultaneously in focus on the sample. Further, offset beams may be generated by any method known in the art such as, but not limited to, any diffraction order of an optical element.

It is noted herein that the one or more optical elements 109 may be placed in any number of suitable arrangements to simultaneously split the beam 108 into two or more offset beams 111 and rotate the focal plane 306 to overlap the plane of the wafer 112. In one embodiment, the one or more optical elements 109 include a single DOE to split the beam 108 into two or more offset beams 111, rotate the focal plane 306 to overlap the plane of the wafer 112, and further split each of the two or more offset beams into a set of two or more beams. In another embodiment, the one or more optical elements 109 include a first DOE to split the beam 108 into two or more offset beams 111 and rotate the focal plane 306 to overlap the plane of the wafer 112; and a second DOE to further split each of the two or more offset beams into a set of two or more beams. In another embodiment, the one or more optical elements 109 includes a micro-lens assembly to split the beam 108 into two or more offset beams 111 and a DOE to rotate the focal plane 306 to overlap the plane of the wafer 112 and further split each of the two or more offset beams into a set of two or more beams. It is noted herein that the one or more optical elements 109 may be arranged in any order. For example, the one or more optical elements 109 may include a first DOE to rotate the focal plane 306 to overlap the plane of the wafer 112 and a second DOE to split the beam 108 into two or more offset beams 111. It is further noted that the above descriptions of the one or more optical elements 109 are provided merely for illustration and should not be interpreted as limiting.

In one embodiment, the one or more optical elements 109 are configurable such that a tradeoff between the number of offset beams 111 and the power in each of the offset beams 111 may be adjusted. In this way, a tradeoff between the sensitivity and the throughput of the system 100 may be adjusted. For example, a system 100 may include two configurable optical elements 109 including a first 1×2 DOE to split the beam 108 into two offset beams 111 separated in at least the x-direction and rotate the focal plane 306, and a second 7×1 DOE to split each of the two offset beams 111 into seven offset beams 111 separated along the y-direction. In this way, a 7×2 array of offset beams 111 are simultaneously in focus on the sample 112. In one configuration, the power in each offset beam may be doubled by removing the first DOE such that a 7×1 array of offset beams 111 is simultaneously in focus on the sample 112. In another configuration, the power of each beam may be increased by a ratio of 7/3 by replacing the second 7×1 DOE with a 3×1 DOE such that a 3×2 array of offset beams 111 is simultaneously in focus on the sample. In additional configurations, the number of offset beams 111 may be increased.

It is further noted herein that the set of optics of system 100 as described above and illustrated in FIGS. 1 through 3 are provided merely for illustration and should not be interpreted as limiting. It is anticipated that a number of equivalent or additional optical configurations may be utilized within the scope of the present disclosure. It is anticipated that one or more optical elements including, but not limited to circularly symmetric lenses, cylindrical lenses, beam shapers, mirrors, waveplates, polarizers or filters may be placed in the system 100. For example, a cylindrical lens may be placed prior to the beam deflector 106, or alternatively, after the beam deflector 106 in order to modify the spatial profile of the beam 108 on the wafer 112.

It is noted herein that any of the elements in the system 100 may be configured to include one or more coatings, including, but not limited to, anti-reflective coatings or spectrally selective coatings. For example, a spectrally selective coating may be placed on the faces of acousto-optic deflectors 202 and/or 210, one or more lenses included in the lens assembly 206, and/or one or more lenses throughout the system 100 in order to further the spectral content of the beam 102 and/or 108. In another embodiment, anti-reflective coatings may be placed on non-optical elements of the system 100 including an enclosing chamber for the purposes of reducing stray light throughout the system 100.

FIG. 5 describes a flow diagram illustrating a method 500 for generating multiple beams in an oblique multi-beam spot scanning wafer inspection system in accordance with one or more embodiments of the present disclosure. In step 502, a beam of illumination is generated. In step 504, the beam is directed to a surface at an oblique angle, wherein the beam is substantially perpendicular to a first direction on a plane defined by the surface. In step 506, prior to directing the beam, the beam is split into two or more offset beams separated in at least a second direction, wherein the second direction is perpendicular to the first direction. In step 508, prior to directing the beam, the phase characteristics of the two or more offset beams are modified such that the two or more offset beams are simultaneously in focus on the surface.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically interactable and/or physically interacting components and/or wirelessly interactable and/or wirelessly interacting components and/or logically interactable and/or logically interacting components.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the disclosure is defined by the appended claims.

What is claimed is:

1. An oblique angle multi-beam spot scanning wafer inspection system, comprising:
    a beam scanning device configured to scan a beam of illumination along a surface of a sample along a scanning direction;
    an objective lens positioned with an optical axis oriented perpendicular to the scanning direction and further oriented at an oblique angle relative to the surface of the sample; and
    a focus-controlling splitting device positioned between the objective lens and the beam scanning device to split the beam into two or more offset beams separated in at least an offset direction perpendicular to the scanning direction on the surface of the sample, wherein the two or more offset beams include at least a first offset beam and a second offset beam, wherein the first offset beam and the second offset beam are separated in at least the offset direction on the surface of the sample, wherein the focus-controlling splitting device adjusts a focal position of the first offset beam relative to a focal position of the second offset beam along a direction parallel to the optical axis, wherein focal positions of the two or more offset beams correspond to the surface of the sample during a scan.

2. The system of claim 1, wherein the two or more offset beams comprise:
a two-dimensional array of offset beams with two or more staggered rows separated along the offset direction.

3. The system of claim 1, wherein the focus-controlling splitting device includes one or more diffractive optical elements.

4. The system of claim 3, wherein the focus-controlling splitting device includes a diffractive optical element comprising a grating with period T and further comprising defocus wavefront modification of amplitude A,
wherein the diffractive optical element splits the beam into two or more diffracted orders K separated in the offset direction,
wherein the two or more diffracted orders K are simultaneously in focus through the objective lens on the sample during the scan,
wherein the diffractive optical element introduces a phase delay of $K*[2*\pi*x/T+A(x^2+y^2)]$, where $K=0, \pm 1, \pm 2 \ldots$, y corresponds to the scanning direction, and x corresponds to the offset direction.

5. The system of claim 3, wherein at least one of the one or more diffractive optical elements operates in at least one of a reflection or a transmission mode.

6. The system of claim 3, wherein at least one of the one or more diffractive optical elements comprises a holographic grating.

7. The system of claim 1, wherein the focus-controlling splitting device includes one or more refractive optical elements.

8. The system of claim 7, wherein at least one of the one or more refractive optical elements comprises a micro-lens assembly.

9. The system of claim 1, wherein the focus-controlling splitting device includes a first optical element configured to split an incident beam into two or more beams separated in the offset direction and modify the phase characteristics of the two or more beams such that the two or more beams are simultaneously in focus on the sample during the scan, and a second optical element configured to further split an incident beam into two or more beams separated in the scanning direction.

10. The system of claim 1, further comprising one or more detectors positioned to receive light from the sample.

11. The system of claim 1, wherein a spot size of at least one of the two or more offset beams is constant during the scan.

12. The system of claim 1, wherein a detection sensitivity of at least one of the two or more offset beams is constant during the scan.

13. The system of claim 1, wherein the beam scanning system includes at least one of an acousto-optic deflector, an electro-optic beam deflector, a polygonal scanner, a resonant scanner, or a galvanometer scanner.

14. The system of claim 1, wherein the beam scanning system comprises:
an acousto-optic deflector, wherein a transducer coupled to the acousto-optic deflector generates one or more chirp packets of ultrasonic waves with linearly varying frequency that propagate through a solid medium of the acousto-optic deflector, wherein the one or more chirp packets focus at least a portion of a beam of illumination incident on the acousto-optic deflector to a spot that propagates along a line.

15. The system of claim 14, wherein the beam incident on the acousto-optic deflector fully illuminates the solid medium such that the beam simultaneously illuminates the one or more chirp packets.

16. The system of claim 14, wherein the beam scanning system further comprises:
a beam deflector positioned to direct the beam to a chirp packet propagating in the acousto-optic deflector, wherein a size of the beam corresponds to a size of the chirp packet.

17. An apparatus for the generation of spots on an inclined surface, comprising:
a focus-controlling splitting device including one or more optical elements positionable in a beam scanning system prior to a lens oriented at an oblique angle relative to a surface, wherein an optical axis of the lens is perpendicular to a scanning direction on a plane defined by the surface, wherein the focus-controlling splitting device splits a beam into two or more offset beams separated in at least an offset direction, wherein the offset direction is perpendicular to the scanning direction, wherein the two or more offset beams include at least a first offset beam and a second offset beam, wherein the first offset beam and the second offset beam are separated in at least the offset direction on the surface of the sample, wherein the focus-controlling splitting device modifies a focal position of the first offset beam relative to a focal position of the second offset beam along a direction parallel to the optical axis, wherein focal positions of the two or more offset beams correspond to the surface during a scan.

18. The system of claim 17, wherein the two or more offset beams comprise:
a two-dimensional array of offset beams with two or more staggered rows, wherein the two or more staggered rows are separated along the offset direction.

19. The system of claim 17, wherein the focus-controlling splitting device includes one or more diffractive optical elements.

20. The system of claim 19, wherein the focus-controlling splitting device includes a diffractive optical element comprising a grating with period T and further comprising defocus wavefront modification of amplitude A,
wherein the diffractive optical element splits the beam into two or more diffracted orders K separated in the offset direction,
wherein the two or more diffracted orders K are simultaneously in focus on the surface during the scan,
wherein the diffractive optical element introduces a phase delay of $K*[2*\pi*x/T+A(x^2+y^2)]$, where $K=0, \pm 1, \pm 2, \ldots$, y corresponds to the scanning direction and x corresponds to the offset direction.

21. The system of claim 19, wherein at least one of the one or more diffractive optical elements operate in at least one of reflection or transmission modes.

22. The system of claim 19, wherein at least one of the one or more diffractive optical elements comprises a holographic grating.

23. The system of claim 17, wherein the focus-controlling splitting device includes one or more refractive optical elements.

24. The system of claim 23, wherein at least one of the one or more refractive optical elements comprises a micro-lens assembly.

25. The system of claim 17, wherein the focus-controlling splitting device includes a first optical element configured to split an incident beam into two or more beams separated in the offset direction and modify the phase characteristics of the two or more offset beams such that the two or more offset beams are simultaneously in focus on the sample during the scan, and a second optical element configured to split an incident beam into two or more beams separated in the scanning direction.

26. The system of claim 17, wherein a spot size of at least one of the two or more offset beams is constant during the scan.

27. A method for generating multiple beams in an oblique angle multi-beam spot scanning wafer inspection system, comprising:
   generating a beam of illumination;
      splitting the beam into two or more offset beams separated along at least an offset direction, wherein the two or more offset beams include at least a first offset beam and a second offset beam; and
   focusing the two or more offset beams simultaneously on a tilted surface with a diffractive optical element and a lens oriented with an optical axis at an oblique incidence angle relative to the tilted surface, wherein the first offset beam and the second offset beam are separated in at least the offset direction on the surface of the sample, wherein the diffractive optical element includes a curved diffraction grating providing defocus wavefront modification to adjust a focal position of the first offset beam relative to a focal position of the second offset beam along a direction parallel to the optical axis, wherein focal positions of the two or more offset beams correspond to the tilted surface.

28. The method of claim 27, further comprising:
   scanning the two or more offset beams across the tilted surface along a scanning direction perpendicular to the offset direction.

* * * * *